United States Patent
Demin

(10) Patent No.: US 7,278,311 B1
(45) Date of Patent: Oct. 9, 2007

(54) LIQUID LEVEL AND DENSITY MEASUREMENT DEVICE

(75) Inventor: Vitaliy Demin, Saco, ME (US)

(73) Assignee: Franklin Fueling Systems, Inc., Madison, WI (US)

( * ) Notice: Subject to any disclaimer, the term of this patent is extended or adjusted under 35 U.S.C. 154(b) by 0 days.

(21) Appl. No.: 11/472,897

(22) Filed: Jun. 22, 2006

(51) Int. Cl.
*G01F 23/76* (2006.01)
(52) U.S. Cl. .................... 73/322.5; 73/313; 73/291; 73/319
(58) Field of Classification Search ............. 73/291, 73/313, 319, 322.5
See application file for complete search history.

(56) References Cited

U.S. PATENT DOCUMENTS

| 4,155,254 A | 5/1979 | Colditz |
| 4,581,931 A | 4/1986 | Robotti et al. |
| 4,839,590 A | 6/1989 | Koski et al. |
| 5,253,522 A | 10/1993 | Nyce et al. |

FOREIGN PATENT DOCUMENTS

RU    2138028    9/1999

OTHER PUBLICATIONS

International Search Report for PCT/US06/03236 dated May 24, 2006.
Written Opinion of the International Searching Authority for PCT/US06/03236 dated May 24, 2006.

*Primary Examiner*—Hezron Williams
*Assistant Examiner*—Paul M West
(74) *Attorney, Agent, or Firm*—Marshall Gerstein & Borun LLP

(57) ABSTRACT

A liquid level and density measurement device is disclosed. The device comprises an elongated magnetostrictive transducer and at least two transducer magnets embedded into floats that can freely move along a transducer. One float is relatively more sensitive to liquid density variation than the other float. The less sensitive float is used for liquid level measurement and the more sensitive float is used for liquid density measurement. The liquid density float has a lower part completely immersed into a liquid and an upper part partially immersed into a liquid. The upper part is made substantially in the form of a hollow cylinder with an internal diameter larger than the external diameter of the liquid level float. Therefore the liquid density float can move up and down without touching the liquid level float.

7 Claims, 3 Drawing Sheets

FIG. 3A
FIG. 3B
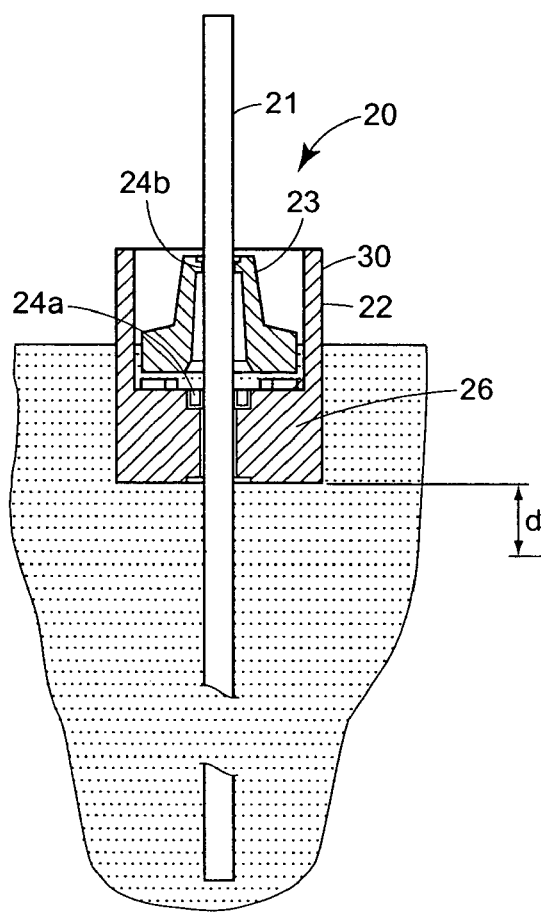
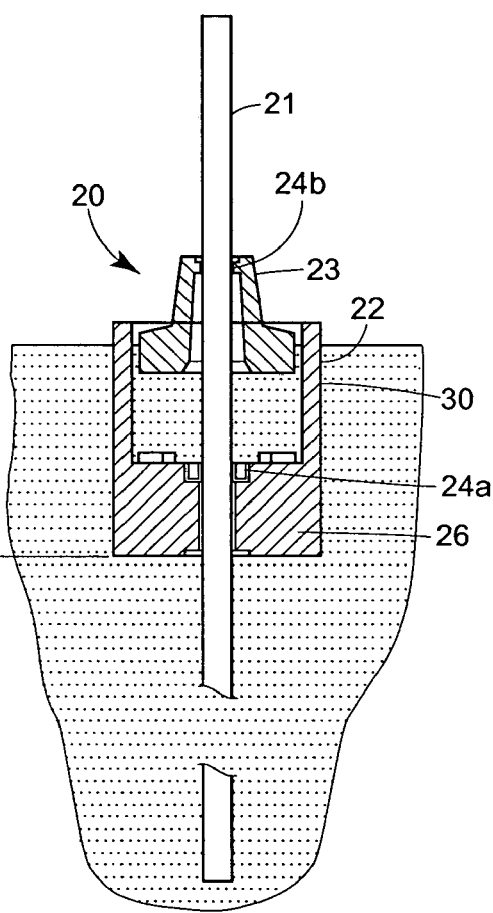

LIQUID LEVEL AND DENSITY MEASUREMENT DEVICE

THE FIELD OF THE INVENTION

This invention relates to a device for measuring the level and density of a liquid in a tank, such as an underground petroleum storage tank.

BACKGROUND OF THE INVENTION

Magnetostrictive transducers are widely used for the liquid level measurement. See, for example, Koski et al., U.S. Pat. No. 4,839,590. Koski et al., discloses a measurement device for precision measurement of a liquid level in an underground storage tank that, in combination with a temperature measurement, allows detecting very small leaks from the tank. There is also a need for an accurate product density measurement in the same containers where the level is being measured.

A widely known method of density measurement is based on the hydrostatic principle that the weight loss of an object in a liquid equals the weight of the liquid displaced. The method is used in hydrometers where a relatively large weighted lower portion of a body is completely immersed into a liquid and a tall narrow upper section with a scale sticks out above the surface. The immersion depth of the hydrometer is in an inverse proportion to the liquid density. The hydrometer will float higher in a heavy liquid and lower in a light liquid. The sensitivity of the hydrometer is in an inverse proportion with a cross section of the upper section. The narrower this part is, the more sensitive the hydrometer is. The measurement range of the hydrometer is in direct proportion with the height of upper part. The taller that part is, the larger measurement range is.

There are also devices that combine level and density measurement in one magnetostrictive transducer. See, for example, Nyce et al., U.S. Pat. No. 5,253,522, and Russian patent RU 2138028.

The device disclosed in the Russian patent, and as generally illustrated in FIGS. 1a, 1b and 1c, includes a liquid density float 17, and a liquid level measurement float (not shown). The level measurement float is relatively less sensitive to liquid density variation and the liquid density float 17 is relatively more sensitive to liquid density variation. The liquid density float 17 is made in the form of an immersed cylinder 16 and four narrow vertical rods 15 that are located on top of the cylinder around its perimeter and extend above the surface. In essence, it is a group of four hydrometers connected together. The diameter of the density float 17 should be large enough to allow the liquid level float to freely move between the rods 15.

Size is one drawback of such a device. As discussed above, magnetostrictive transducers are widely used for leak detection in underground tanks. Such leak detection requires reliable measurement of very small changes of the liquid level, in the range of 0.001 inches (0.025 mm) or less. To achieve this type of resolution, the float for the level measurement should be heavy enough and therefore large enough to overcome the friction between the float and the body of the transducer, otherwise an effect known as "stiction" can mask a leak. At the same time, standard openings in the tanks for the transducer installation are typically four inches (100 mm) in diameter or less, which limits the permitted diameter of the float. To increase the tank opening size would be expensive.

To be able to combine level and density measurement into one transducer installed into a standard tank opening, without compromising leak detection capabilities, requires a density float to take as small portion of the opening diameter as possible and leave sufficient room for the level float.

SUMMARY OF THE INVENTION

In accordance with the invention, shape of the density measurement float allows minimizing its diameter. This is achieved by making the upper part of the density float substantially in the form of a hollow cylinder with an external diameter smaller than the opening diameter of the tank and an internal diameter larger than external diameter of the level float.

BRIEF DESCRIPTION OF THE DRAWINGS

FIGS. 3a and 3b are side sectional views of the liquid level and density measurement device of FIGS. 2a and 2b, illustrating the float positions in liquids of different densities.

DESCRIPTION OF THE PREFERRED EMBODIMENT

While this invention is susceptible of embodiment in many different forms, there will be described herein in detail, a specific embodiment thereof with the understanding that the present disclosure is to be considered as an exemplification of the principles of the invention and is not intended to limit the invention to the specific embodiment illustrated.

Figure 1A:
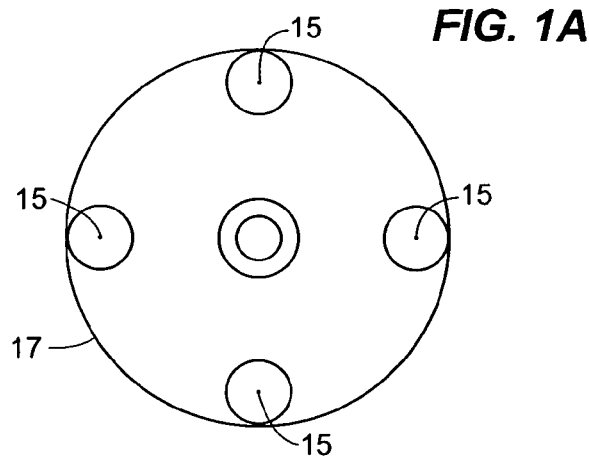
FIGS. 1a, 1b and 1c are respective top, side and perspective views of a prior art liquid density measurement device.
Figure 1B:
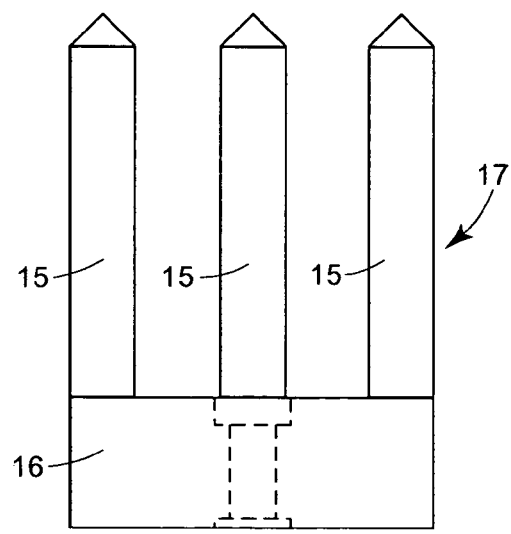
Figure 1C:
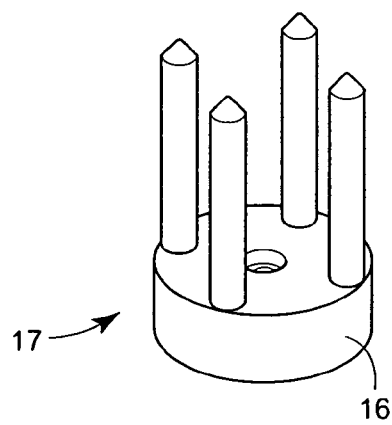
Figure 2A:
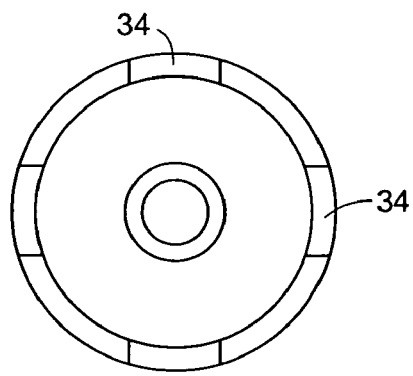
FIGS. 2a, 2b and 2c are respective top, side and perspective views of a density float of the liquid level and density measurement device according to the invention.
Figure 2B:
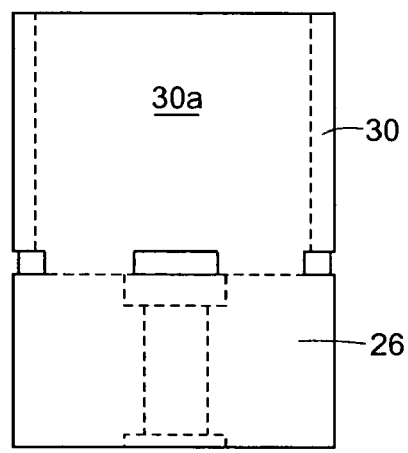
Figure 2C:
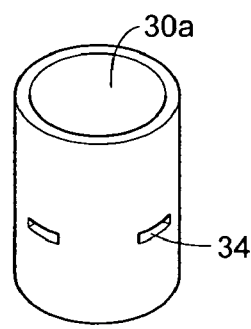

A liquid level and density measurement device, generally designated 20, is illustrated in FIGS. 2a, 2b, 2c, 3a and 3b. The liquid level and density measurement device 20 comprises a conventional, elongated magnetostrictive transducer 21 and first and second transducer magnets 24a and 24b. The first transducer magnet 24a is embedded into a liquid density float 22, which is relatively more sensitive to liquid density variations. The second transducer magnet 24b is embedded in a liquid level float 23, which is relatively less sensitive to liquid density variations. The floats 22, 23 can freely move along the transducer 21. The liquid level float 23 is used for liquid level measurement, and the liquid density 22 is used for liquid density measurement.

The liquid density float 22 has a lower part 26 completely immersed into a liquid 28 and an upper part 30 partially immersed into the liquid 28. The upper part 30 is made substantially in the form of a hollow cylinder, with an internal diameter defining a cavity 30a. The internal diameter of the cavity 30a is dimensioned larger than the external diameter of the liquid level float 23. Therefore the liquid density float 22 can move up and down without touching the liquid level float 23.

The liquid density float 22 is shown in a relatively more dense liquid in FIG. 3a and in a relatively less dense liquid in FIG. 3b. The difference in height "d" is indicative of the relative difference of the densities of the two liquids.

The liquid density float 22 preferably is made of a low density material with a ballast at the bottom. The lower part 26 preferably has a diameter of approximately 95 mm. The upper part preferably has an outer diameter of 95 mm and an inner diameter of approximately 82 mm.

The liquid level float is preferably made of a low density material. It has a diameter preferably of approximately 72 mm.

Openings 34 are provided through the upper part 30 to permit fluid to flow into the cavity 30a.

Because the generally cylindrical upper part 30 of the liquid density float 22 has circumferentially more mass than does the prior art liquid density float, its diameter can be reduced to permit insertion through a typical four inch tank opening.

The upper part 30 of the liquid density float 22 may be other than cylindrical. For example it may have a taper due to its formation during a molding process.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the Claims.

The invention claimed is:

1. A device for placement in a tank of liquid for determining the level and density of the liquid in the tank, the device comprising:
    a liquid density sensing float having a lower base portion and an upper portion extending substantially continuously about a periphery of the base portion and defining a cavity;
    a liquid level sensing float disposed in the cavity; and
    circuitry for determining the height of the density sensing float and the level sensing float, wherein the density sensing float and the level sensing float include a magnet and the circuitry includes a magnetostrictive transducer.

2. The device of claim 1 wherein the density sensing float and the level sensing float include an aperture to slidably receive the magnetostrictive transducer.

3. The device of claim 1 wherein the density sensing float is dimensioned to fit through a four inch opening into the tank.

4. A device for placement in a tank of liquid for determining the level and density of the liquid in the tank, the device comprising:
    a liquid density sensing float having a lower base portion and an upper portion extending substantially continuously about a periphery of the base portion and defining a cavity;
    a liquid level sensing float disposed in the cavity; and
    circuitry for determining the height of the density sensing float and the level sensing float, wherein the upper portion is substantially cylindrical.

5. A device for placement in an underground liquid storage tank, the device to determine the level and density of liquid in the tank, the device comprising:
    a magnetostrictive transducer to be generally vertically disposed in the tank;
    a liquid density sensing float having a lower base portion and a generally cylindrical upper portion extending substantially continuously about a periphery of the base portion and defining a cavity, wherein the density sensing float includes a magnet and the base portion has a bore to slidably receive the transducer;
    a liquid level sensing float slidably disposed in the cavity and having a bore to slidably receive the transducer, wherein the level sensing float includes a magnet; and
    circuitry coupled to the transducer for determining the position of the magnets relative to the transducer.

6. A system for measuring the height and density of a liquid comprising:
    an underground storage tank containing the liquid and having a nominally four inch opening;
    a magnetostrictive transducer generally vertically disposed in the tank;
    a liquid density sensing float having a lower base portion and a generally cylindrical upper portion extending substantially continuously about a periphery of the base portion and defining a cavity, wherein the density sensing float includes a magnet and the base portion has a bore slidably receiving the transducer;
    a liquid level sensing float slidably disposed in the cavity and having a bore slidably receiving the transducer, wherein the level sensing float includes a magnet; and
    circuitry coupled to the transducer for determining the position of the magnets relative to the transducer.

7. A liquid level and density measurement device comprising an elongated magnetostrictive transducer and at least two transducer magnets embedded into a liquid density float and a liquid level float and spaced along a transducer, wherein the liquid density float is more sensitive to liquid density variations than the liquid level float, and the liquid density float has a lower part completely immersed into a liquid wherein the improvement comprises:
    an upper part of the liquid density float partially immersed into the liquid is made substantially in the form of hollow cylinder with an internal diameter larger than the external diameter of the liquid level float.

* * * * *

UNITED STATES PATENT AND TRADEMARK OFFICE
CERTIFICATE OF CORRECTION

PATENT NO. : 7,278,311 B1 Page 1 of 1
APPLICATION NO. : 11/472897
DATED : October 9, 2007
INVENTOR(S) : Vitaliy Demin It is certified that error appears in the above-identified patent and that said Letters Patent is hereby corrected as shown below:

Title Page, Insert Item

(60)  --Related U.S. Application Data
Continuation of Application No. PCT/US06/0326,
filed on January 30, 2006--.

Signed and Sealed this

Twentieth Day of May, 2008

JON W. DUDAS
*Director of the United States Patent and Trademark Office*